US009662489B1

(12) United States Patent
Cargill, III

(10) Patent No.: US 9,662,489 B1
(45) Date of Patent: May 30, 2017

(54) ELECTRO-HYDRO MASSAGE DEVICE

(71) Applicant: George S. Cargill, III, Longboat Key, FL (US)

(72) Inventor: George S. Cargill, III, Longboat Key, FL (US)

(*) Notice: Subject to any disclaimer, the term of this patent is extended or adjusted under 35 U.S.C. 154(b) by 0 days.

(21) Appl. No.: 15/367,924

(22) Filed: Dec. 2, 2016

(51) Int. Cl.
| | | |
|---|---|---|
| *A61N 1/32* | (2006.01) | |
| *A61N 1/18* | (2006.01) | |
| *H05K 5/06* | (2006.01) | |
| *A61H 33/00* | (2006.01) | |
| *A61N 1/04* | (2006.01) | |
| *A61F 7/00* | (2006.01) | |
| *G08B 5/36* | (2006.01) | |

(52) U.S. Cl.
CPC ............ *A61N 1/322* (2013.01); *A61F 7/0053* (2013.01); *A61H 33/0087* (2013.01); *A61H 33/0095* (2013.01); *A61N 1/0476* (2013.01); *G08B 5/36* (2013.01); *H05K 5/069* (2013.01); *A61F 2007/0059* (2013.01); *A61F 2007/0087* (2013.01); *A61H 2201/0153* (2013.01); *A61H 2201/0207* (2013.01); *A61H 2201/0214* (2013.01); *A61H 2201/10* (2013.01)

(58) Field of Classification Search
None
See application file for complete search history.

(56) References Cited

U.S. PATENT DOCUMENTS

| | | | | |
|---|---|---|---|---|
| 4,033,356 A | * | 7/1977 | Hara | .................... A61N 1/0452 607/150 |
| 8,182,473 B2 | * | 5/2012 | Altshuler | ........... A45D 26/0061 606/13 |
| 9,108,055 B1 | | 8/2015 | Tellenbach | |
| 9,220,896 B2 | | 12/2015 | Bachinski et al. | |
| 9,411,636 B1 | | 8/2016 | Nathanson et al. | |
| 2015/0272775 A1 | | 10/2015 | Fahey et al. | |
| 2016/0235258 A1 | * | 8/2016 | Zhao | ........................ A47K 7/04 |

OTHER PUBLICATIONS

S. Rush, J. A. Abildskov, and R.McFee, "Resistivity of Body Tissues at Low Frequencies," Circulation Research, vol. 12, Jan. 1963, pp. 40-50, Dallas, TX.

* cited by examiner

*Primary Examiner* — Brian T Gedeon

(57) ABSTRACT

An electro-hydro massage device enhances the therapeutic benefits of electrical nerve and muscle stimulation by incorporating simultaneous tactile and thermal stimulation from water flow, using a hand-held source of electric current and water flow, in contact with the user's skin. The water flow also reduces the skin's resistance to electrical current and provides warming or cooling to complement and enhance effects of the electrical stimulation. The treatment surface of the hand-held electro-hydro massage device contacts the user's skin and contains two or more electrodes and one or more sources of water flow. The electrically conductive electrodes imbedded in the treatment surface are connected to a battery-powered electrical source with controls to select the source voltage amplitude, voltage frequency, pulse frequency, and other characteristics to achieve the desired physiological effects. The device is connected to a water source with selectable temperature and flow rate, with aeration to facilitate more gentle and uniform water flow over the treatment area.

12 Claims, 11 Drawing Sheets

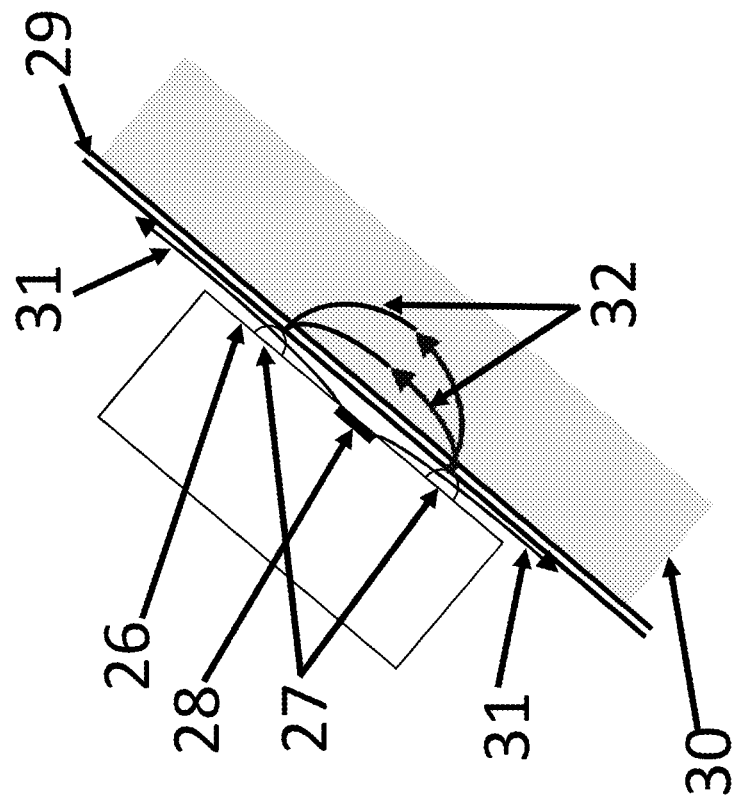
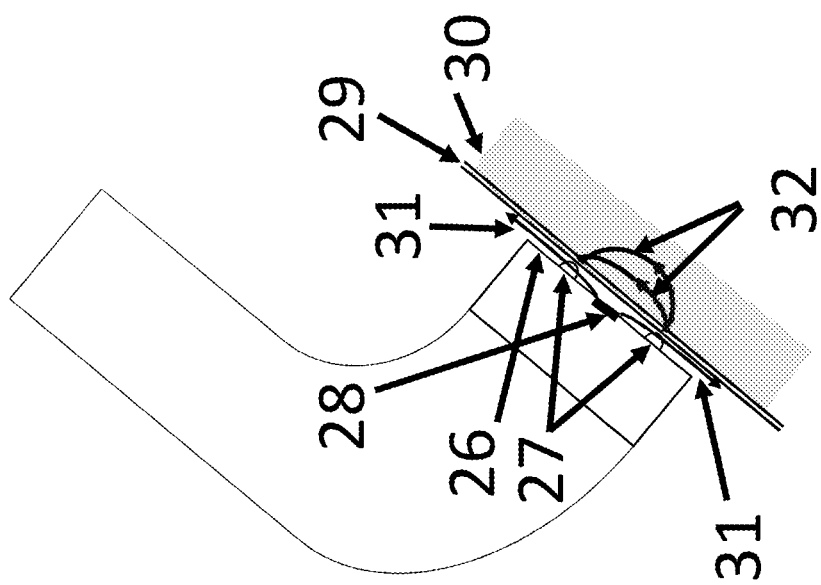

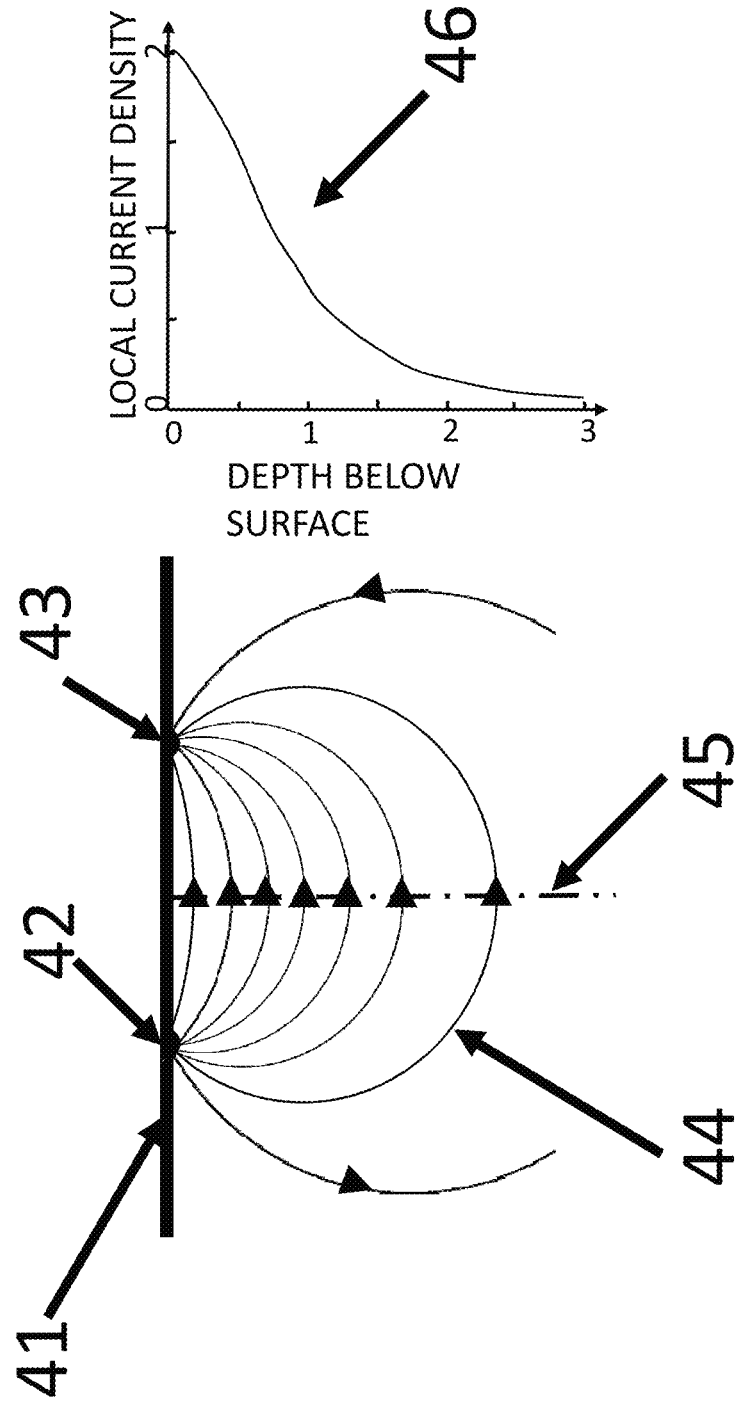

| BAT1 | 9V | |
|---|---|---|
| C1 | 0.11 μ | 124Hz |
| C2 | 0.22μ | 62Hz |
| C3 | 0.44 μ | 31Hz |
| C4 | 0.001μ | |
| C5 | 3.5 μ | 3.8Hz |
| C6 | 7 μ | 1.9Hz |
| C7 | 14 μ | 0.95Hz |
| C8 | 0.001μ | |
| C9 | 0.1 μ | |
| CREG1 | 10ma | curr. reg. diode |
| CREG2 | 10ma | curr. reg. diode |
| IC1 | NE555 | 31-124Hz output |
| IC2 | NE555 | 0.95-3.8Hz output |
| NMOSFET1 | IRFH5306 | |
| NMOSFET2 | IRFH5306 | |
| R1 | 5.1k | |

| R2 | 51k | |
|---|---|---|
| R3 | 100k | |
| R4 | 3.1k | |
| R5 | 1k var | Vout 0-70V ptp |
| R6 | 1k | |
| R7 | 22 | |
| R8 | 5.1k | |
| R9 | 51k | |
| R10 | 100k | |
| R11 | 100 | |
| R12 | 5k | |
| R13 | 22 | |
| R14 | 26k | |
| SW1 | SPST | on-off switch |
| SW2 | SP3POS | voltage freq. sel. sw. |
| SW3 | SP3POS | pulse freq. sel. sw. |
| T1 | 12V:120V | |

FIG. 16

ELECTRO-HYDRO MASSAGE DEVICE

FIELD OF INVENTION

The present invention provides an electro-hydro massage device for electrical nerve and muscle stimulation with simultaneous tactile and thermal stimulation by water flow.

BACKGROUND OF THE INVENTION

Transcutaneous electrical nerve stimulation (TENS) and electrical muscle stimulation (EMS) are well known techniques for pain reduction and improved muscle performance and recovery. Currently available TENS and EMS devices introduce electrical current to nerves and muscles through conductive pads adhesively attached to the user's skin near the area to be treated, often coated with an electrically conductive gel, or through two or more conductive electrodes on the face of a hand-held device in contact with the user's skin in the treated area. In both cases, the conductive pads or electrodes are connected to a source of electricity with voltage, frequency, and other characteristics selected to achieve the desired physiological effects. Hydro-massage is also a well know technique for muscle relaxation and reduction of muscle-related aches and pains. Hydro-massage is carried out using water jets in Jacuzzi-type tubs for full or partial body immersion, or using hand-held water jets in shower-type enclosures. Benefits of hydro-massage result from both tactile and thermal stimulation by the flowing water.

SUMMARY OF INVENTION

The present invention is a device that enhances the therapeutic benefits of electrical nerve and muscle stimulation by incorporating simultaneous tactile and thermal stimulation from water flow, using a hand-held source of electric current and water flow, in contact with the user's skin. The local water flow and electrical current simultaneously provide tactile, thermal and electrical stimulation. The water flow also moistens the skin, reducing resistance to electrical current flow, and it provides warming or cooling to complement and enhance effects of the electrical stimulation. The treatment surface of the hand-held electro-hydro-massage device contacts the user's skin and contains two or more electrodes and one or more sources of water flow. The treatment surface may be composed of a rigid, electrically insulating material, or it may consist of a flexible, compressible, electrically insulating material which facilitates contact with nonplanar body surfaces. The electrically conductive electrodes imbedded in the treatment surface are connected to an electrical source with controls to turn the source on and off, to select the source voltage amplitude, and perhaps also to select the voltage frequency, pulse frequency, and other characteristics chosen to achieve the desired physiological effects. The device is connected to a water source with selectable temperature and flow rate, in some embodiments with water flow aeration to facilitate more gentle and uniform water flow over the treatment area. The electrical source is battery-powered and is either incorporated in the hand-held device or is a separate module connected to the hand-held device by a flexible cable. For ease of use, the device may have indicator lights to show the battery status and the voltage amplitude, voltage frequency, and pulse frequency, as well as other electrical parameters that have been selected.

BRIEF DESCRIPTION OF THE FIGURES

FIG. 6 is a side view of the hand-held device in contact with the body area being treated. and FIG. 7 is a magnified view of the treatment surface and treated area. Both FIG. 6 and FIG. 7 show paths of water flow between the treatment surface and the user's skin, as well as electrical current paths through the user's underlying muscles and nerves.

FIG. 8 shows the current density distribution calculated for a two-electrode configuration, assuming uniform electrical conductivity within the subcutaneous tissue. It shows the current density distribution using current flux lines, where the smaller spacing between the flux lines indicates higher current density, and the direction of the flux lines shows the direction of current flow, at an instant when the left electrode has a positive voltage and the right electrode has a negative voltage.

FIG. 9 shows a line plot of the local current density versus depth below the surface, calculated for current passing through the plane midway between the electrodes.

FIG. 16 lists component values and ranges of electrical output characteristics.

DETAILED DESCRIPTION OF THE PREFERRED EMBODIMENTS

Figure 1:
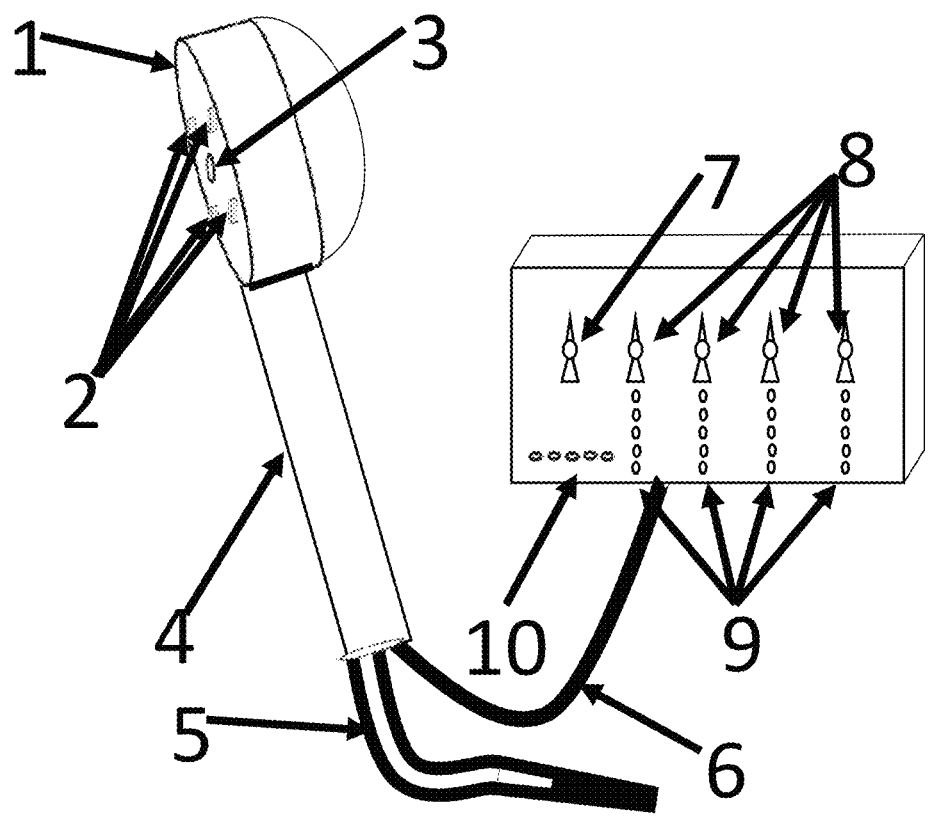
FIG. 1 is an isometric view of an embodiment where the electrical source and controls are in a module separate from the hand-held electro-hydro-massage device and where there are four electrodes and one water flow aperture.

FIG. 1 is an isometric view of an embodiment of an electro-hydro-massage device of the present invention that includes water flow for simultaneous hydro-massage. For reasons discussed below, the massage device has characteristics that make it suitable for providing electric, tactile and thermal transcutaneous stimulation of nerves and muscles. The device has a set of electrodes 2 connected to an electrical supply 10. The electrodes are imbedded in a treatment surface 1 consisting of either a rigid, electrically insulating material, or a flexible, compressible, electrically insulating material which facilitates contact with nonplanar body surfaces. Also imbedded in the treatment surface is a water flow aperture 3 connected by a flexible hose 5 to a flow rate and temperature controlled water source. The hand-device is sealed against water intrusion, and the water path from the supply hose 5 to the water flow aperture 3 is secured to prevent water leakage within the device. For the embodiment shown in FIG. 1, the battery-powered electrical supply 10 is separate from the hand-held device but is connected to it by a two-conductor flexible electrical cable 6. The electrical supply is also sealed against water intrusion. The electrical supply contains an on-off switch 7 and switches or potentiometers 8 for selecting different characteristics of the electricity supplied to the electrodes 2, such as voltage, voltage frequency, and pulse frequency, chosen to achieve the desired physiological effects. The electrical supply may also contain arrays of lights 9 to indicate the battery state and the values of electrical parameters chosen with the selector switches or potentiometers.

Figures 2, 3:
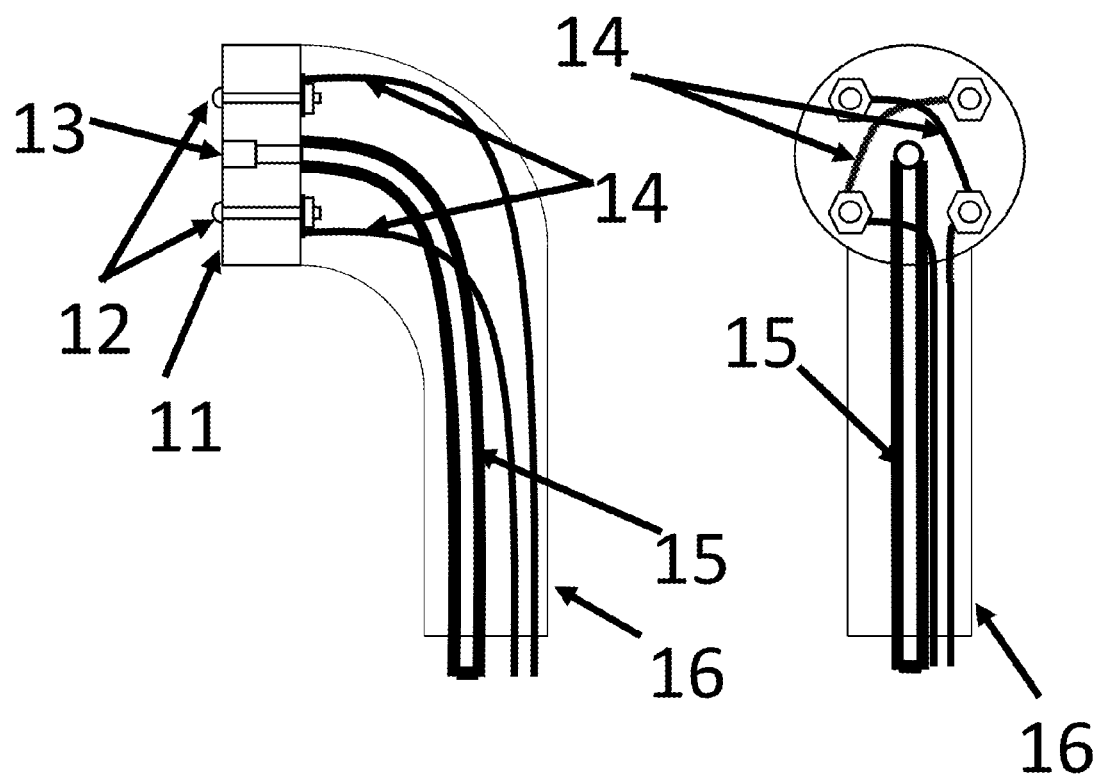
FIG. 2 is a section view through the side of the device.
FIG. 3 is a section view through the back of the device, for an embodiment where the electrical source and controls are in a module separate from the hand-held device, showing two of the four electrodes in the side view and the backs of the four electrodes in the back view, with wires connecting the electrodes to the electrical source, which is not shown. Also shown in the figure is the hose running from the water flow aperture to the water source, which is not shown.

FIG. 2 and FIG. 3 illustrate further details for the embodiment shown in FIG. 1. The electrodes 12 embedded in the treatment surface 11 extend above this surface. A preferred shape of the electrodes is hemispherical. The electrode shape and extension above the treatment surface are chosen to permit water flow between the treatment surface and the user's skin, and to provide a smooth, corner-free electrode surface that can easily slide along the skin when the device is moved from one treatment location to another. The embodiment shown in FIG. 1, FIG. 2 and FIG. 3 employs four electrodes, in a square array, with diagonally opposed electrodes electrically joined 14, and each joined pair of electrodes connected to one of the two conductors of the flexible cable extending from the hand-held device to the electrical supply 10 in FIG. 1.

Figure 4:
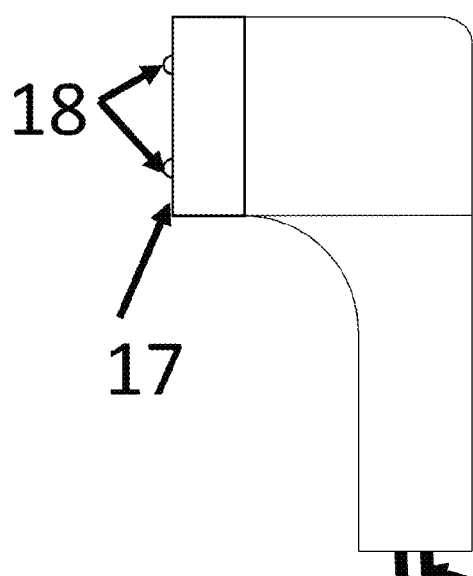
FIG. 4 is a side view and FIG. 5 is a rear view for an embodiment where the electrical source and controls are incorporated in the hand-held device, showing electrical controls, indicator lights, access to the battery compartment, the water flow control, and the hose from the device to the water supply, not shown.
Figure 5:
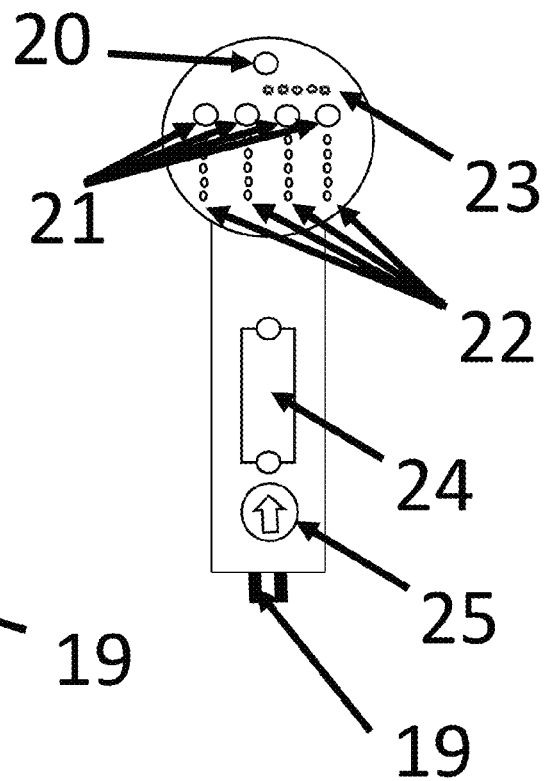

FIG. 4 is a side view and FIG. 5 is a rear view of an embodiment that includes water flow for simultaneous hydro-massage and in which the electrical supply and associated battery 24, on-off switch 20, controls 21 and indicator lights 22, 23 are incorporated within the hand-held device. For this embodiment the water flow rate control 25 is also part of the hand-held device, with the water supplied by a flexible hose 19 connecting the device to a temperature-controlled water source. The hand-held device is sealed to prevent water intrusion.

FIG. 6 describes the interaction between the electro-hydro-massage device employing water flow and the user's skin 29 and subcutaneous nerves and muscles 30. FIG. 7 is an enlargement of the interaction region. Water from the device's water flow aperture 28 passes between the treatment surface 26 and the user's skin 29, causing the skin in contact with the electrodes 27 to remain moist, thereby reducing the skin's electrical resistance to current flow 32, and also providing tactile and thermal stimulation to the user's skin 29 and subcutaneous nerves and muscles 30 in the treatment area. Also shown, schematically, are paths of electrical current flow 32 from the electrodes 27, through the moistened skin 29, and through the subcutaneous nerves and muscles 30. The subcutaneous current distribution depends on spacing and arrangement of the electrodes, and on the electrical characteristics of the skin and the electrical characteristics and distribution of subcutaneous tissues.

FIG. 8 shows the current density distribution calculated for two-electrodes 42 and 43 in contact with the skin 41, assuming uniform electrical conductivity within the subcutaneous tissue. The current density distribution is represented by current flux lines 44, where the smaller spacing between the flux lines indicates higher current density, and the direction of the flux lines shows the direction of current flow, at an instant when the left electrode 42 has a positive voltage and the right electrode 43 has a negative voltage. FIG. 9 shows a line plot 46 of the local current density versus depth below the surface, calculated for current passing through the plane 45 midway between the electrodes. The depth scale for the plot is in units corresponding to half the electrode spacing. The current density scale is in units of Amperes per unit area for an electrode spacing of 1 and an electrode current of 1 A. As seen in FIG. 8, current densities are highest adjacent to each electrode, and the current densities decrease with distance away from each electrode, and as seen in FIG. 9 current densities decrease with depth into the subcutaneous nerves and muscle. For an electrode spacing of one inch, the local current density decreases at the midpoint between the electrodes by half for a depth of about 0.4 inches below the skin surface. Increasing the electrode spacing increases the depth of current penetration.

Assuming uniform electrical conductivity, or resistivity, within subcutaneous tissue is valid only when current passes through large volumes, effectively averaging the conductivities of different muscles and other organs. For example, Rush et al. (1963) reported large anisotropy in electrical resistivity of muscle, citing a longitudinal resistivity of 2.52 ohm-meter and a transverse resistivity of 5.63 ohm-meter for heart muscle. Similar electrical anisotropies are expected for other types of muscle. A particular benefit of the four-electrode electro-hydro-massage device shown in FIG. 1, FIG. 2 and FIG. 3, resulting in the subcutaneous current distribution shown in FIG. 11, is that current paths are multidirectional, so that the lower resistivity longitudinal muscles would be stimulated, regardless of the orientation of the electrode array.

Figures 10, 11:
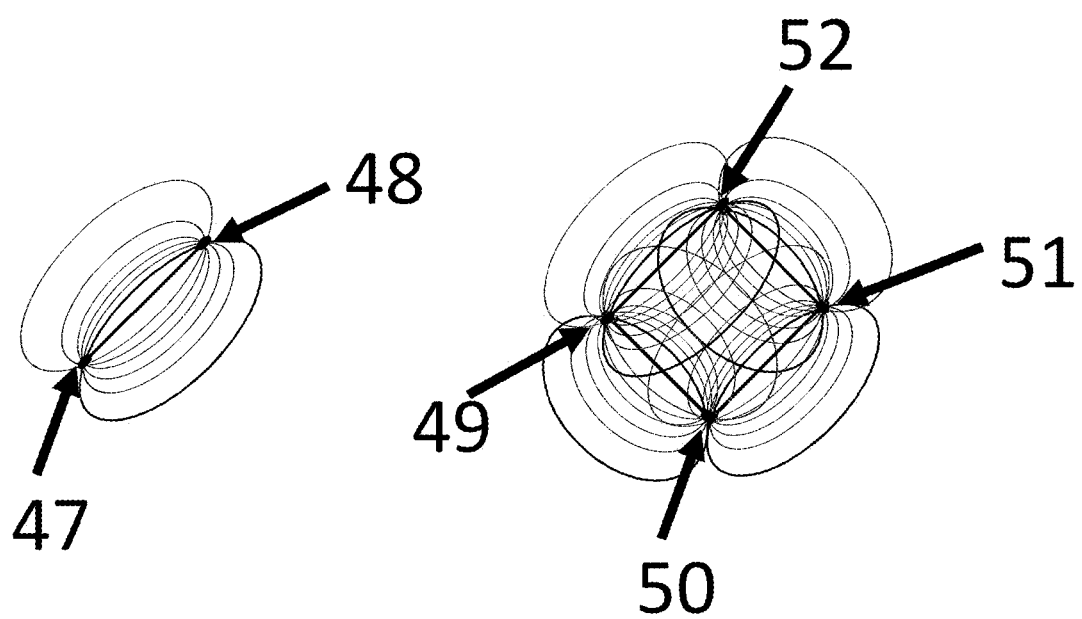
FIG. 10 shows the current density distribution in the near surface region viewed from above, for a two electrode configuration, like that shown in FIG. 8.
FIG. 11 shows the current density distribution for a four electrode configuration, like that shown in FIG. 1, FIG. 2, and FIG. 3. As in FIG. 8, the current density is represented by current flux lines, where the smaller spacing between the flux lines indicates higher current density. For the four electrode configuration, with diagonally opposite electrodes having the same polarity applied voltage, the current density is a superposition of that for the two electrode pairs.

FIG. 10 shows the current density distribution in the near surface region viewed from above, for a configuration of two electrodes 47 and 48, and FIG. 11 shows the current density distribution for a configuration of four electrodes 49, 50, 51, 52. As in FIG. 8, the current density is represented by current flux lines, where the smaller spacing between the flux lines indicates higher current density. For the four electrode configuration, with one pair of diagonally opposite electrodes 49 and 51 having the same polarity applied voltage, and the other pair of diagonally opposed electrodes 50 and 52 having the opposite polarity applied voltage, the current density is a superposition of that for the four electrode pairs.

Figure 12:
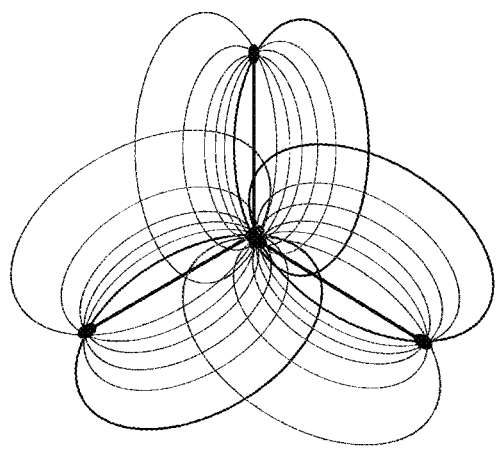
FIG. 12 shows the current density distribution in the near surface region viewed from above for a four electrode configuration with the three outer electrodes having the same polarity and the center electrode having the opposite polarity.
Figure 13:
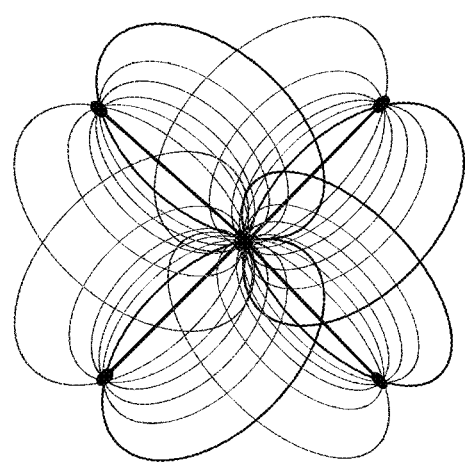
FIG. 13 shows the current density distribution for a five electrode configuration with the four outer electrodes having the same polarity and the center electrode having the opposite polarity. As in FIG. 8, the current density is represented by current flux lines, where the smaller spacing between the flux lines indicates higher current density.

FIG. 12 shows the current density distribution in the near surface region viewed from above, for a configuration of four electrodes with the outer three electrodes at the corners of a triangle and electrically joined together and with the inner electrode at the center of the triangle, having an opposite polarity from the outer three electrodes; and FIG. 13 shows the current density distribution for a configuration of five electrodes with the outer four electrodes at the corners of a square and electrically joined together and with the inner electrode at the center of the square, having an opposite polarity from the outer four electrodes. These electrode configurations, like those in FIG. 11 could be used for the electro-hydro massage device, with the four and five electrode configurations providing multidirectional current paths that can better stimulate nerves and muscles oriented in different directions with respect to the hand-held massage device.

Figure 14:
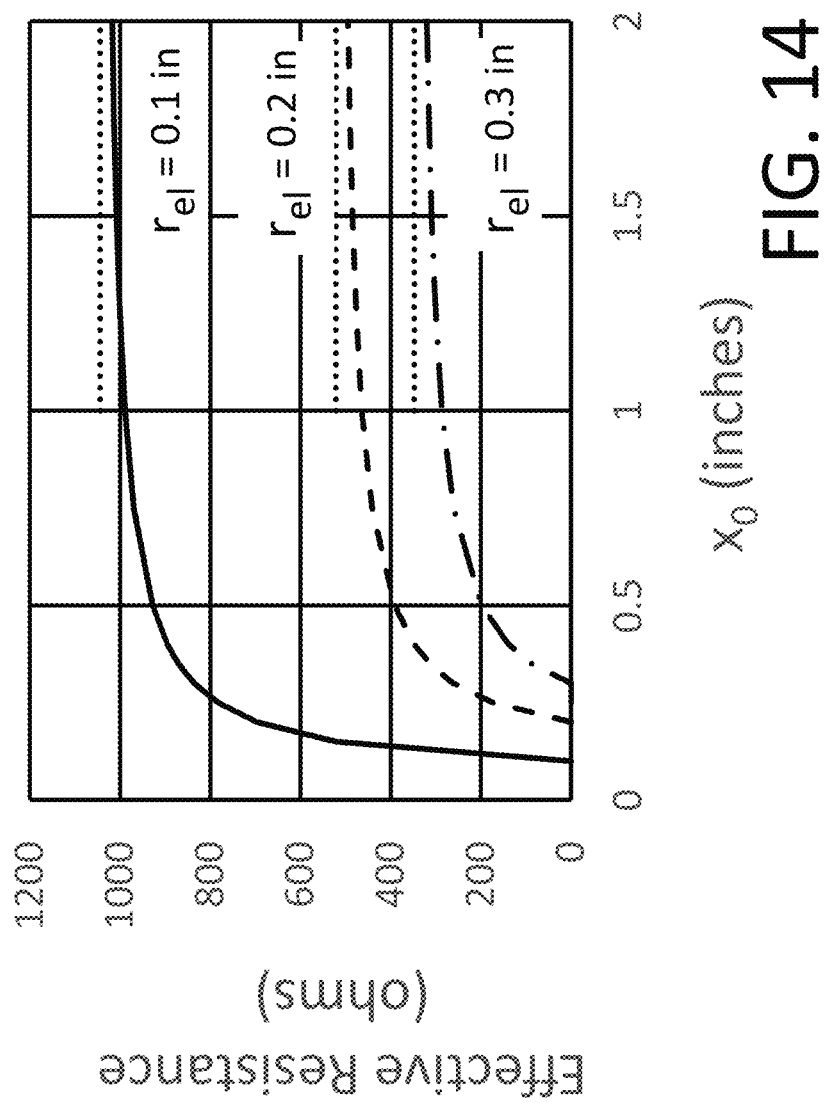
FIG. 14 shows a line plot of effective resistance versus electrode spacing for a two electrode configuration for three different electrode radii, neglecting skin resistance and assuming uniform resistivity of 8.3 ohm-meter for the subcutaneous flesh.

FIG. 14 shows line plots of effective resistance in ohms versus electrode spacing for a two-electrode configuration, neglecting skin resistance and assuming uniform conductivity, 0.12 S/m, for the subcutaneous flesh, for hemispherical electrodes of radii $r_{el}$ of 0.1 in, 0.2 in, and 0.3 in. The horizontal axis corresponds to values of $x_0$ in inches, with electrode spacing of $2x_0$. The horizontal dotted lines indicate the asymptotic values of effective resistance for each electrode radius for $x_0 \gg r_{el}$. FIG. 14 illustrates that the effective resistance decreases with increases in electrode radius, and that the effective resistance increases little for electrode spacings larger than 1 in for the range of electrode radii shown. Including skin resistance would increase the effective resistance values, but the effective resistance would still decrease with increases in electrode radius, and the effective resistance would become less dependent on electrode spacing.

A key feature of the electro-hydro-massage device is use of flowing water to maintain skin moisture in the treatment area, which significantly reduces the skin's electrical resistivity. Although skin electrical resistivity, or conductivity, is expected to vary for different areas of the body, it is helpful to consider the sheet conductivity value quoted by Rush et al. (1963) for stratum corneum $\sigma_\square = 0.5$ S/m$^2$ corresponding to a sheet resistivity of $\rho_\square = 2.0$ ohm-m$^2$. Thoroughly moistening of skin is expected to increase its conductivity by at least two times, or to reduce its resistivity to half of the dry skin value. For a hemispherical electrode of radius $r_{el} = 0.25$ in ($5.9 \times 10^{-3}$ m), the corresponding electrode area is $A = 2.2 \times 10^{-4}$ m$^2$, and the electrode-to-skin resistance would be $R = \rho_\square/A = 9.0 \times 10^3$ ohms for dry skin, or $4.5 \times 10^3$ ohms for moist skin. The combined electrode-to-skin resistance for two electrodes, passing current into and out of the skin, would be $2R = 2\rho_\square/A = 1.8 \times 10^4$ ohms for dry skin, or $9.0 \times 10^3$ ohms for moist skin. Comparing these electrode-to-skin resistance values with those shown for subcutaneous flesh in FIG. 14 for $r_{el} = 0.2$ in and 0.3 in, which are smaller than 500 ohms, it is clear that most of the electrical resistance, and most of the voltage drop and absorption of electrical energy, occur as electric current passes through the skin rather than through subcutaneous flesh for the electrode dimensions proposed for the electro-hydro-massage device. Moistening the skin reduces the skin-related voltage drop and electrical energy absorption, leaving more electrical energy for stimulation of subcutaneous nerves and muscles, and reducing the possibility of electrical damage to the skin in contact with the electrodes.

Figure 15:
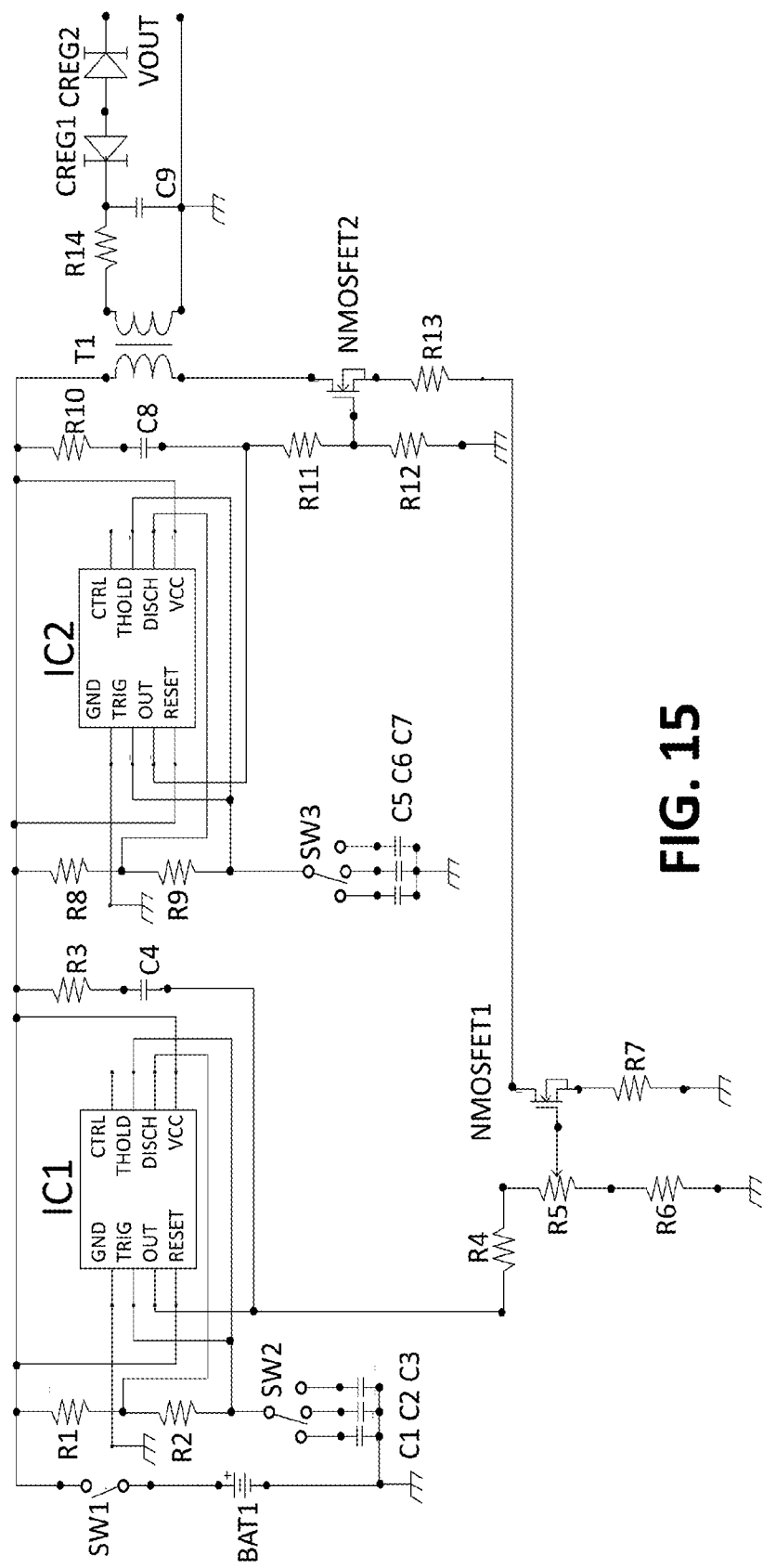
FIG. 15 shows a schematic diagram for a battery-powered electrical supply suitable for use with an electro-hydromassage device. This power supply provides a selectable voltage amplitude, voltage frequency and pulse frequency, depending on the potentiometer and switch settings.

FIG. 15 shows a schematic diagram for a battery-powered electrical supply suitable for use with an electro-hydro massage device. This power supply provides a pulsed AC voltage, with selectable voltage frequency, pulse frequency, and voltage amplitude depending on the switch and potentiometer settings. FIG. 16 lists component values and ranges of electrical output characteristics. The power supply shown in FIG. 15 with the component values listed in FIG. 16 can supply voltage frequencies of 31 Hz, 62 Hz and 124 Hz; pulse frequencies of 0.95 Hz, 1.9 Hz, and 3.8 Hz; and voltage amplitudes from 0V to 140V peak-to-peak for different settings of SW2, SW3, and R5. Current regulation diodes CREG1 and CREG2 limit the output current to 10 ma peak-to-peak. Other voltage frequencies, pulse frequencies, voltage amplitudes and maximum output currents could be provided by using other component values in the power supply circuit shown in FIG. 15, as well as by using other power supply circuits.

Figure 17:
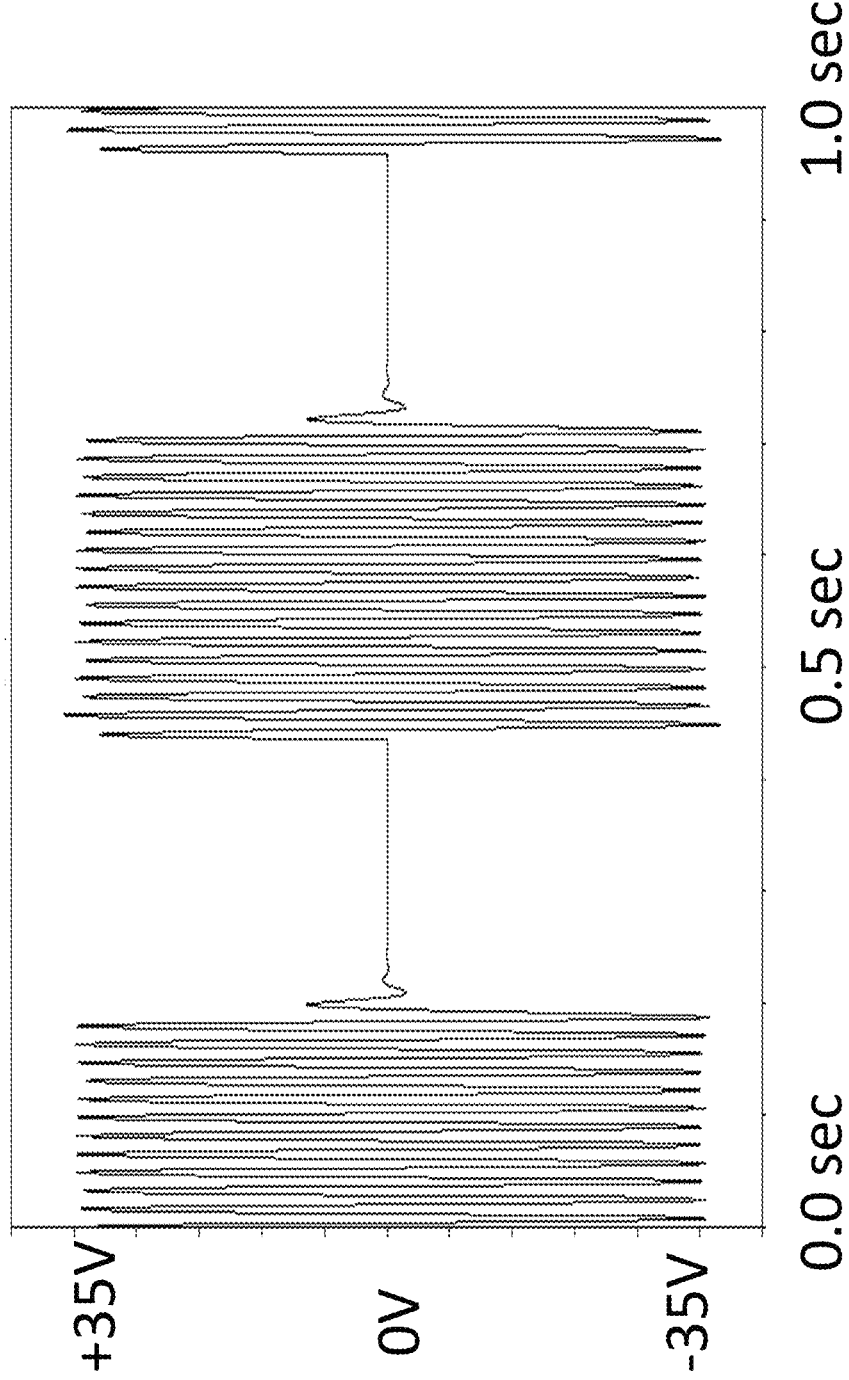
FIG. 17 shows the output voltage from the circuit shown in FIG. 15 for midpoint voltage frequency, pulse frequency and voltage amplitude settings.

FIG. 17 shows the output voltage from the circuit shown in FIG. 15 for midpoint voltage frequency, pulse frequency and voltage amplitude settings, corresponding to voltage frequency of 62 Hz, pulse frequency of 1.9 Hz, and voltage amplitude of 70V peak-to-peak.

What I claim is:

1. A hand-held device for electrical nerve and muscle stimulation, with simultaneous tactile and thermal stimulation and reduction of skin electrical resistance by water flow, comprising:
   a hand-held assembly with a handle and with a treatment surface composed of an electrically insulating material;
   one or more pairs of electrically conductive electrodes imbedded in and passing through the treatment surface;
   one or more water flow apertures imbedded in and passing through the treatment surface;
   a battery powered electrical source; and
   electrodes connected to the electrical source with a switch to turn the source on and off.

2. A device described in claim 1 with an electrical source having controls to select the voltage and other characteristics of the electricity at the electrodes, which may include the voltage amplitude, voltage frequency, and pulse frequency, to achieve the desired physiological effects.

3. A device described in claim 1 that is sealed against water intrusion.

4. A device described in claim 1 with electrodes on the treatment surface having smooth, corner-free, approximately semi-ellipsoidal shapes, to facilitate movement of the treatment surface across the user's skin and to permit water flow between the treatment surface and the user's skin.

5. A device described in claim 1 having four electrodes in a square array with diagonally opposite electrodes electrically joined together and with each joined pair of electrodes connected to one of the conductors from the electrical source.

6. A device described in claim 1 having four electrodes, with three in a triangular array and with one at the center of the triangle, with the three outer electrodes connected to one of the conductors from the electrical source, and with the central electrode connected to the other conductor from the electrical source.

7. A device described in claim 1 having five electrodes, with four in a square array and with one at the center of the square, with the four outer electrodes connected to one of the conductors from the electrical source, and with the central electrode connected to the other conductor from the electrical source.

8. A device described in claim 1 connected to a water source by a flexible hose, with selectable temperature and flow rate.

9. A device described in claim 1 with one or more water flow apertures incorporating aeration to facilitate more gentle and uniform water flow between the treatment surface and the user's skin in the treatment area.

10. A device described in claim 1 with an electrical source incorporated in the hand-held device.

11. A device described in claim 1 with an electrical source in a separate module, sealed against water intrusion, connected to the device by a flexible cable with two conductors through which electricity passes from the electrical source to the electrodes on the treatment surface.

12. A device described in claim 1 having indicator lights to show the battery status and the voltage amplitude, voltage frequency, and pulse frequency that have been selected.

* * * * *